United States Patent [19]

Sudilovsky

[11] 4,346,106
[45] Aug. 24, 1982

[54] METHOD FOR INHIBITING ONSET OF MIGRAINE HEADACHES WITH NADOLOL COMPOSITIONS

[75] Inventor: Abraham Sudilovsky, Lawrenceville, N.J.

[73] Assignee: E. R. Squibb & Sons, Inc., Princeton, N.J.

[21] Appl. No.: 277,378

[22] Filed: Jun. 25, 1981

Related U.S. Application Data

[63] Continuation-in-part of Ser. No. 263,656, May 14, 1981, abandoned.

[51] Int. Cl.$^3$ .................... A61K 31/22; A61K 31/135
[52] U.S. Cl. .................................... 424/311; 424/330
[58] Field of Search ................................ 424/311, 330

[56] References Cited

U.S. PATENT DOCUMENTS 3,935,267  1/1976  Houck et al. .................... 424/248.53
4,029,676  6/1977  Houck et al. ........................ 424/280

OTHER PUBLICATIONS

Advertisement from *Diversion Vacation Planner*, Spring 1981, pp. 27 and 28, Regarding Use of Inderal to Prevent Migraine Headaches.

*Primary Examiner*—Stanley J. Friedman
*Attorney, Agent, or Firm*—Lawrence S. Levinson; Burton Rodney

[57] ABSTRACT

A method is provided for inhibiting onset of migraine headaches with nadolol or esters of nadolol.

6 Claims, No Drawings

METHOD FOR INHIBITING ONSET OF MIGRAINE HEADACHES WITH NADOLOL COMPOSITIONS

RELATED APPLICATION

This application is a continuation-in-part of application Ser. No. 263,656, filed May 14, 1981, now abandoned.

FIELD OF THE INVENTION

The present invention relates to a method for inhibiting onset of migraine headaches by administering nadolol or an ester thereof.

DESCRIPTION OF THE INVENTION

In accordance with the present invention, a method is provided for preventing or inhibiting onset of migraine headaches in mammalian species wherein a therapeutically effective amount of nadolol or an ester thereof is systemically, e.g. orally or parenterally, administered.

The term "nadolol" as employed herein refers to the beta blocker 2,3-cis-1,2,3,4-tetrahydro-5-[2-hydroxy-3-(tert-butylamino)propoxy]-2,3-naphthalenediol (and pharmaceutically acceptable acid-addition salts thereof)

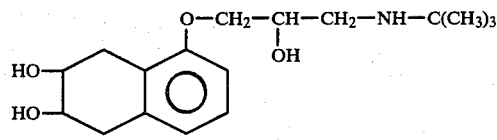

which is disclosed in U.S. Pat. Nos. 3,935,267 and 3,982,021, the aforementioned patents being incorporated herein by reference.

Esters of nadolol included herein are the mono-, di- and tri-esters (and pharmaceutically acceptable acid-addition salts thereof).

The di-esters have the structure

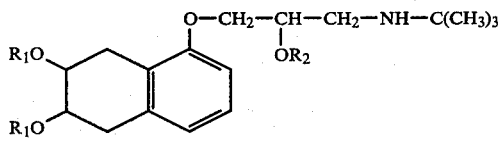

wherein both $R_1$ groups are acryl, preferably acetyl, and $R_2$ is hydrogen, and are disclosed in U.S. Pat. No. 4,029,676 which is incorporated herein by reference.

Esters of nadolol wherein both $R_1$ groups are hydrogen and $R_2$ is acyl (mono-ester), preferably acetyl, and wherein both $R_1$ groups are acyl, preferably acetyl, and $R_2$ is acyl, preferably acetyl (tri-esters) are disclosed in British patent specification No. 1,559,987 which is incorporated herein by reference.

In carrying out the method of the present invention, the nadolol or nadolol ester or a physiologically acceptable acid-addition salt may be administered to mammalian species, such as monkeys, dogs, cats, rats, etc. and as such may be incorporated in a conventional dosage form, such as a tablet, capsule, elixir, injectable or the like along with the necessary carrier material, excipient, lubricant, buffer, or the like. Oral dosage forms are preferred, although parenteral forms are quite satisfactory as well. Single or divided doses of from about 1 to about 320 mg, preferably from about 60 to about 240 mg one to four times daily, optimally in a single dose, may be administered in dosage forms as described above.

The following working Examples represents a preferred embodiment hereof.

EXAMPLE

A nadolol formulation suitable for oral administration in the prevention of migraine headaches is set out below.

| Ingredient | mg/tablet |
| --- | --- |
| Nadolol | 40 |
| Magnesium stearate | 1 |
| Microcrystalline cellulose | 72 |

The nadolol is blended with the microcrystalline cellulose in a Hobart-type mixer for 5 minutes. Thereafter, the magnesium stearate is added with mixing for 2–3 minutes. The final mix is compressed in a Strokes D3 tablet press to form a 40 mg tablet which is used for preventing migraine headaces.

What is claimed is:

1. A method for inhibiting onset of migraine headaches in a mammalian species which comprises systemically administering to a mammalian host susceptible to migraine headaches and in need of such treatment nadolol or an ester thereof or a pharmaceutically acceptable acid-addition salt of said nadolol or ester thereof in a dosage of from about 60 to about 240 mg in a single dose per day.

2. The method as defined in claim 1 wherein said nadolol or ester thereof is administered orally or parenterally.

3. The method as defined in claim 1 wherein said ester is a mono-, di- or tri-ester.

4. The method as defined in claim 3 wherein said ester is a monoacetate, diacetate or triacetate.

5. The method as defined in claim 1 wherein said nadolol or ester thereof is admixed with a pharmaceutically acceptable carrier therefor.

6. The method as defined in claim 1 wherein said nadolol or ester thereof is in the form of a pharmaceutically acceptable acid-addition salt thereof.

* * * * *